United States Patent

Sugihara et al.

[11] 4,330,554
[45] May 18, 1982

[54] SPIROBENZOFURANONE COMPOUNDS

[75] Inventors: Hirosada Sugihara, Osaka; Masazumi Watanabe, Kawanishi; Mitsuru Kawada, Hyogo; Isuke Imada, Osaka, all of Japan

[73] Assignee: Takeda Chemical Industries, Ltd., Osaka, Japan

[21] Appl. No.: 257,317

[22] Filed: Apr. 17, 1981

Related U.S. Application Data

[63] Continuation-in-part of Ser. No. 115,548, Jan. 25, 1980, Pat. No. 4,284,644, which is a continuation-in-part of Ser. No. 968,520, Dec. 11, 1978, abandoned.

[30] Foreign Application Priority Data

Apr. 23, 1980 [GR] Greece ................................. 61757
Mar. 30, 1981 [JP] Japan ................................ 56/48285

[51] Int. Cl.³ .................... C07D 307/94; A61K 31/34
[52] U.S. Cl. ..................................... 424/285; 549/345
[58] Field of Search .................... 260/346.22; 424/285

[56] References Cited

U.S. PATENT DOCUMENTS 4,105,670  8/1978  Nogushi et al. ............ 260/326.11 R

FOREIGN PATENT DOCUMENTS 3084  7/1979  European Pat. Off. .

OTHER PUBLICATIONS

Okitsu et al., Heterocycles, vol. 6, No. 11, (1977).
Donnelly et al., Chem. and Ind., (1967), pp. 1402–1403.

*Primary Examiner*—Henry R. Jiles
*Assistant Examiner*—Bernard Dentz
*Attorney, Agent, or Firm*—Wegner & Bretschneider

[57] ABSTRACT

Novel spirobenzofuranone compounds of the formula:

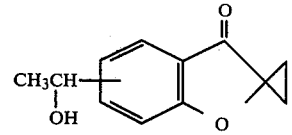

have gastric secretion inhibitive, antiinflammatory and analgesic activities, and are of value as drugs.

7 Claims, No Drawings

SPIROBENZOFURANONE COMPOUNDS

This application is a continuation-in-part of application Ser. No. 115,548, filed Jan. 25, 1980 now U.S. Pat. No. 4,284,644, which is a continuation-in-part of application Ser. No. 968,520, filed Dec. 11, 1978, now abandoned.

This invention relates to spirobenzofuranone compounds and use of said compounds.

The present spiro compounds have the following formula (I):

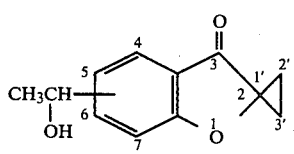

Referring to the above formula (I), the 1-hydroxyethyl group may be present at any position substitutable on the benzene ring and a preferred position is the 5- or 7-position.

The compound (I) of the present invention can be produced, for example, by subjecting a compound of the formula (II):

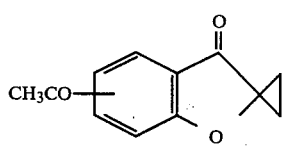

to reduction.

The reduction is normally carried out in a suitable solvent. While any solvent that will not interfere with the reaction may be employed, examples of the solvent include ethyl ether, tetrahydrofuran, dioxane, dimethoxyethane, dichloromethane, pyridine, isopropyl alcohol, etc. and a mixture thereof. The reduction is advantageously carried out by using a reducing agent such as a metal borohydride (e.g. sodium borohydride or potassium borohydride). The reaction temperature is normally about −70° C. to +40° C., preferably −15° C. to +20° C., although the reaction may be conducted at higher or lower temperatures if it is desired to prevent reduction of the carbonyl group at the 3-position and to control the reaction velocity.

The contemplated compound (I) produced in the foregoing manner can be isolated from the reaction mixture and purified by conventional procedures (e.g. distillation, column chromatography, etc.). The compound (I) has optical isomers based on its asymmetric carbon atom and said isomers are included in the scope of the present invention.

The spiro compounds (I) according to this invention are new compounds which exhibit gastric secretion inhibitive, antiinflammatory, analgesic and other effects in mammals (e.g. man, rat, mouse, guinea-pig, dog and pig), for instance, the compound (I) having 1-hydroxyethyl at the 5-position shows strong protective effect against gastric mucosal erosion in rats at a dose of 50 mg/kg according to the method by Robert et al. [Gastroenterology, 77, 433 (1979)], and it is less toxic.

Therefore, they are of value as antiulcer, antiinflammatory, analgesic and as drugs for the management of peptic ulcer, acute or chronic gastritis, lumbago, arthritis and other diseases. Management of a peptic ulcer in accordance with the present invention includes both the prophylactic administration of the spiro compounds (I) to prevent the outbreak of an ulcer in an ulcer prone patient, as well as the treatment of an existing peptic ulcer. In such medicinal applications, each compound (I) can be safely administered orally or parenterally, either as it is or as formulated with pharmaceutically acceptable carriers or diluents known per se into suitable dosage forms such as tablets, powders, capsules, injections and suppositories. While the recommended dosage depends on the subject, condition, route of administration, etc., the normal oral dosage for the treatment of peptic ulcer or acute or chronic gastritis is about 1 mg. to 20 mg. as compound (I) per kg body weight per dose, to be given once to 3 times daily.

The starting compound (II) which is employed in the practice of this invention can be prepared by the procedure described in European Patent Publication No. 3084 published on July 25, 1979, or any process analogous thereto.

The following reference and working examples are given to describe this invention in further detail but should not be considered as limiting the scope of this invention in any way.

REFERENCE EXAMPLE 1

To a mixture of methyl 3-acetylsalicylate (5.8 g) and potassium carbonate (10.4 g) in acetone (200 ml) was added α-bromo-γ-butyrolactone (12.5 g) under stirring, and the mixture was refluxed for 11 hours. The insolubles were filtered off and the filtrate was concentrated under reduced pressure. The residue was subjected to chromatography on silica gel eluting with chloroform. By the above procedure, there was obtained α-[(6-acetyl-2-methoxycarbonylphenyl)oxy]-γ-butyrolactone as pale yellow oil.

Infra red absorption spectrum (IR)$\nu_{max}^{film}$ cm$^{-1}$: 1780 (γ-lactone), 1720 (COOCH$_3$), 1690 (COCH$_3$); Elemental analysis, for $C_{14}H_{14}O_6$; Calcd.: C, 60.43; H, 5.07; Found: C, 60.21; H, 5.02.

REFERENCE EXAMPLE 2

A mixture of α-[(6-acetyl-2-methoxycarbonylphenyl)oxy]-γ-butyrolactone (3.5 g), 1,8-diazabicyclo[5,4,0]-7-undecene (0.14 g) and sodium chloride (1.1 g) in N,N-dimethylformamide (66.5 ml) was stirred at 150°–160° C. for 5 hours. The solvent was distilled off under reduced pressure and the residue was subjected to chromatography on silica gel. The fraction eluted with dichloromethane was recrystallized from CHCl$_3$-hexane to give 7-acetylspiro[benzo[b]furan-2(3H), 1'-cyclopropane]-3-one (0.22 g) as colorless needles melting at 114°–115° C.

Elemental analysis, for $C_{12}H_{10}O_3$; Calcd.: C, 71.28; H, 4.99; Found: C, 71.39; H, 4.96.

REFERENCE EXAMPLE 3

A mixture of α-[(4-acetyl-2-methoxycarbonylphenyl)oxy]-γ-butyrolactone (2.8 g), 1,8-diazabicyclo[5,4,0]-7-undecene (0.056 g), sodium chloride (0.6 g) and N,N-dimethylformamide (28 ml) was heated at 150°–155° C. for 4 hours. The solvent was removed in vacuo and the resulting residue was dissolved in ethyl acetate. The ethyl acetate solution was washed with water and dried. The residue obtained by removal of the solvent in vacuo was chromatographed on silica gel. The fraction eluted with dichloromethane was crystallized from ethanol to give 5-acetylspiro[benzo[b]furan-2(3H), 1'-cyclopropane]-3-one (1.15 g) as colorless crystals.

IR$\nu_{max}^{KBr}$ cm$^{-1}$: 1700, 1680 (CO, COCH$_3$). NMR (CDCl$_3$)δ: 1.70 (4H, q. J=7 Hz, CH$_2$), 2.62 (3H, s, COCH$_3$), 7.20 (1H, d, J=9 Hz, aromat.H), 8.27, 8.30 (1H, dd, J=9 Hz, aromat.H), 8.29 (1H, d, J=2 Hz, aromat.H).

EXAMPLE 1

To a well stirred solution of 5-acetylspiro[benzo[b]furan-2(3H), 1'-cyclopropane]-3-one (1 g) in tetrahydrofuran (25 ml) and isopropanol (3 ml) was added portionwise NaBH$_4$ (0.9 g) cooling at −50° C. The reaction mixture was then stirred at room temperature for 30 minutes, followed by dilution with ice-water, which was neutralized with aqueous ammonium chloride. The aqueous solution was extracted with ethyl acetate. The extract was washed with water and dried. The residue obtained by removal of the solvent was chromatographed on silica gel, eluting with CHCl$_3$. The product was distilled under reduced pressure to give 5-(1-hydroxyethyl)spiro[benzo[b]furan-2(3H), 1'-cyclopropane]-3-one as colorless oil. b.p. 0.05 mmHg: 110° C. (bath temperature). IR$\nu_{max}^{film}$ cm$^{-1}$: 3350(OH), 1710 (CO). NMR (CDCl$_3$)δ: 1.45 (3H, d, J=6 Hz, CH$_3$), 1.62 (4H, q, J=3 Hz, CH$_2$), 3.33 (1H, b, OH), 4.83 (1H, q, J=6 Hz, CH), 6.97 (1H, d, J=9 Hz, aromat.H), 7.55 (2H, m, aromat.H).

Elemental analysis, for C$_{12}$H$_{12}$O$_3$; Calcd: C, 70.57; H, 5.92; Found: C, 70.47; H, 6.05.

EXAMPLE 2

By a similar procedure to that of Example 1, 7-acetylspiro[benzo[b]furan-2(3H), 1'-cyclopropane]-3-one was reacted to give 7-(1-hydroxyethyl)spiro[benzo[b]furan-2(3H), 1'-cyclopropane]-3-one.

IR$\nu_{max}^{film}$ cm$^{-1}$: 3400 (OH), 1700 (CO).

Elemental analysis, for C$_{12}$H$_{12}$O$_3$; Calcd.: C, 70.57; H, 5.92; Found: C, 70.36; H, 5.89.

EXAMPLES OF PREPARATIONS READY FOR ADMINISTRATION

When the compound of this invention is intended for use as an anti-ulcer drug, types of suitable preparations can be exemplified as follows.

1. Injectable solution

In 2 g of polyoxyethylene hydrogenated ricinolate is dissolved with warming 0.2 g of the compound of Example 2. To the solution are added 0.4 g of monosodium phosphate and 0.1 g of disodium phosphate to adjust the pH about 6. There are further added 0.9 g of sodium chloride and 1 g of benzyl alcohol, and then distilled water is added to make the whole volume 100 ml. The mixture is submitted to the step of filling containers therewith, followed by sealing and heat sterilization to prepare an injectable solution.

2. Soft capsule

| Compound of Example 1 | 50 mg |
|---|---|
| Corn oil | 110 mg |
| Total | 160 mg |

The above ingredients are mixed to make a solution and then soft capsules are filled with the solution in a conventional manner.

What is claimed is:

1. A compound of the formula:

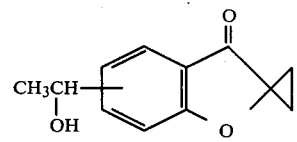

2. The compound according to claim 1, which is 5-(1-hydroxyethyl)spiro[benzo[b]furan-2(3H), 1'-cyclopropane]-3-one.

3. The compound according to claim 1, which is 7-(1-hydroxyethyl)spiro[benzo[b]furan-2(3H), 1'-cyclopropane]-3-one.

4. A pharmaceutical composition for managing peptic ulcer which comprises, as an active ingredient, an effective amount of a compound of the formula:

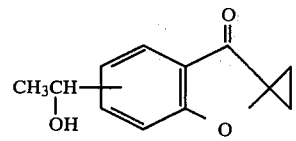

and a pharmaceutically acceptable carrier or diluent therefor.

5. A method of managing peptic ulcer in a patient which comprises administering to said patient a compound of the formula:

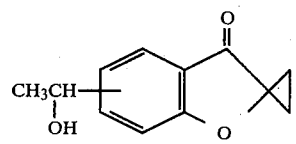

said compound being administered in an amount effective to manage peptic ulcer in said patient.

6. The method according to claim 5, wherein the compound is 5-(1-hydroxyethyl)spiro[benzo[b]furan-2(3H), 1'-cyclopropane]-3-one.

7. The method according to claim 5, wherein the compound is 7-(1-hydroxyethyl)spiro[benzo[b]furan-2(3H), 1'-cyclopropane]-3-one.

* * * * *